United States Patent [19]

Mehl

[11] Patent Number: 4,487,209
[45] Date of Patent: Dec. 11, 1984

[54] BIOPSY NEEDLE

[75] Inventor: Donald N. Mehl, Minnetonka, Minn.

[73] Assignee: Creative Research and Manufacturing Inc., Minnetonka, Minn.

[21] Appl. No.: 468,147

[22] Filed: Feb. 22, 1983

Related U.S. Application Data

[63] Continuation of Ser. No. 244,015, Mar. 16, 1981, abandoned.

[51] Int. Cl.³ ............................................. A61B 10/00
[52] U.S. Cl. .................................................. 128/754
[58] Field of Search ............ 128/221, 272.3, 751–754, 128/347; 403/348, 349; 285/396, 402; 604/272

[56] References Cited

U.S. PATENT DOCUMENTS

| | | | |
|---|---|---|---|
| 2,219,089 | 10/1940 | Everett | 604/272 |
| 2,850,007 | 9/1958 | Lingely | 128/754 |
| 3,330,268 | 7/1967 | Goldsmith | 128/753 |
| 3,628,524 | 12/1971 | Jamshidi | 128/347 |
| 3,633,580 | 1/1972 | Knox | 128/347 |
| 3,995,619 | 12/1976 | Glatzer | 128/754 |
| 4,020,837 | 5/1977 | Larson | 128/272.3 |
| 4,266,555 | 5/1981 | Jamshidi | 128/753 |
| 4,305,180 | 12/1981 | Schwartz | 285/396 |
| 4,314,565 | 2/1982 | Lee | 128/753 |
| 4,403,617 | 9/1983 | Tretinyak | 128/754 |

Primary Examiner—C. Fred Rosenbaum
Assistant Examiner—J. L. Kruter
Attorney, Agent, or Firm—Hugh D. Jaeger

[57] ABSTRACT

Biopsy needle for bone marrow biopsies or the like including a cannula, a cannula housing supporting the cannula, and a stylet including a stylet cap supporting the stylet wherein the stylet engages into the cannula in a predetermined relationship and the stylet cap interlocks to the cannula housing. The biopsy needle is constructed to be either disposable or reusable depending upon the cannula housing and stylet cap material. The cannula housing includes vertical wings extending outwardly from the housing for engagement with the palm of a physician's hand, a cannula having formed ends which engage and secure into the cannula housing, and an elongated button extending outwardly from the top of the cannula housing for detent locking with the stylet cap providing for alignment of the stylet to the cannula of the biopsy needle. The end of the cannula is uniquely formed in a swaging, bevel and grinding, and buffing process providing a sharp knife edge. The stylet includes a longitudinal member having a ground and buffed beveled end maintaining a knife-sharp edge around the tip, and the other end of the stylet is bent and molded into the stylet cap where the stylet cap includes a spring detent locking groove for interlocking with the button of the cannula housing. The stylet cap is rounded at the top and includes vertical grooves for gripping during locking and unlocking. The stylet inserts into the cannula and with a twist locks about the top of the cannula with a positive digital sensory feedback signal to the physician.

10 Claims, 5 Drawing Figures

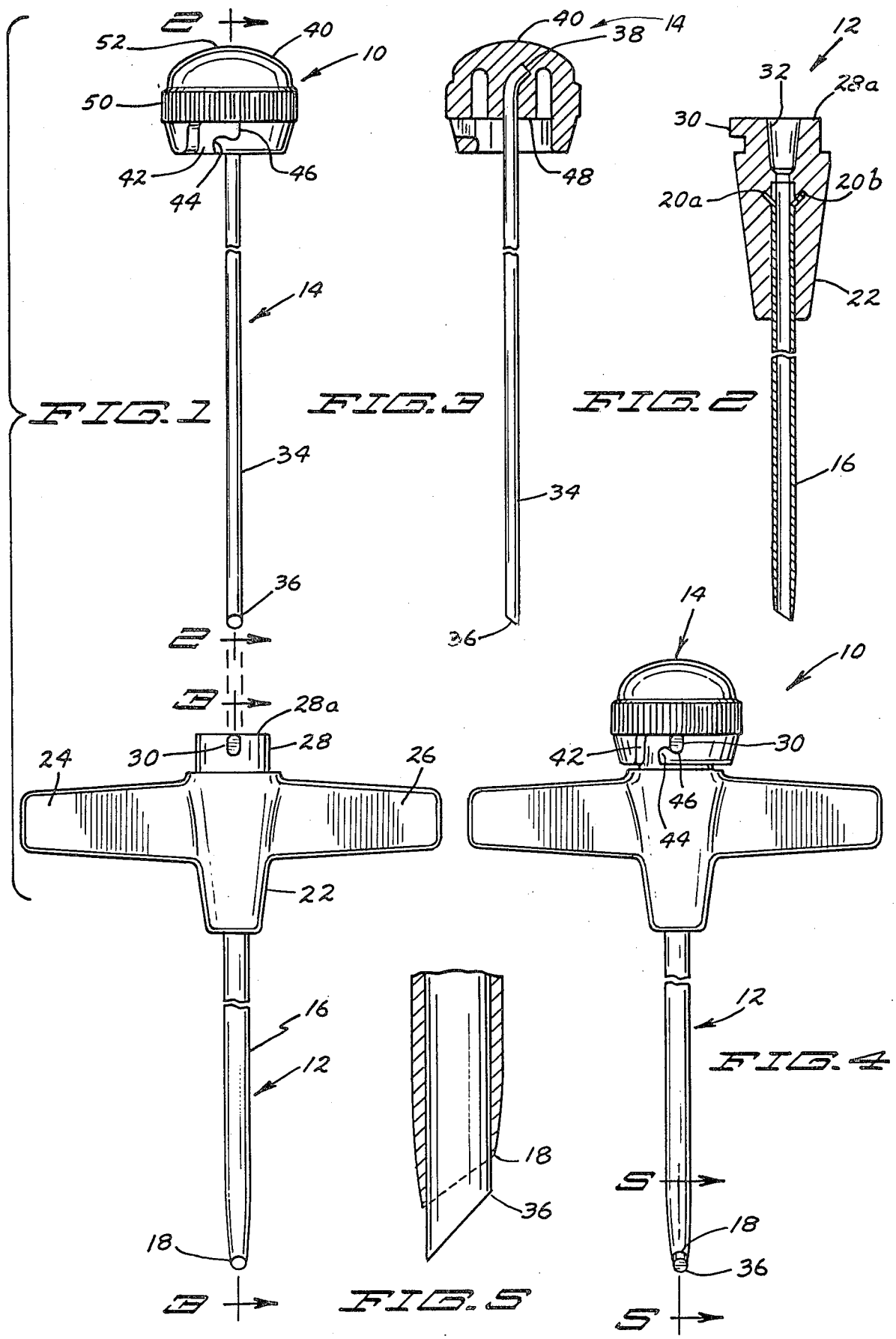

BIOPSY NEEDLE

This application is a continuation of Ser. No. 244,015, Mar. 16, 1981, abandoned.

CROSS REFERENCES TO CO-PENDING APPLICATIONS

This application is also related to Biopsy Needle, Ser. No. 354,421, filed Mar. 3, 1982, assigned to the same assignee. This application is also related to Bone Marrow Aspiration Needle, Ser. No. 354,421, filed Dec. 24, 1981, assigned to the same assignee.

BACKGROUND OF THE INVENTION

1. Field of the Invention—The present invention pertains to a surgical instrument and, more particularly, pertains to a bone marrow biopsy needle which can be either disposable or reusable.

2. Description of Prior Art—The prior art biopsy needles have all presented some type of drawbacks when used by the physician or surgeon, and which are particularly less than desirable. Some prior art instruments are disposable and cast with very few structural details attended to, with the result that the interlocking between the stylet and the cannula provides for considerable play and the instrument can come apart in the user's hands, resulting in injury not only to the patient but more so to the user by the sharp metal edges poking upwards into the physician's hands. Other prior art devices have some form of interlocking structure but the interlocking structure is not positive, resulting in play between the cannula and stylet during the process of incision into the patient resulting in considerable discomfort. Other types of prior art structures have numerous components which during surgery are not practical in utilization by the user due to the screwing and unscrewing of the fittings.

More importantly, all of the prior art devices have grips which do not really fit into the physician's hand to provide for positive gripping by the physician but have grips which are required to be engaged by the physician in a negative way making the process of biopsy as uncomfortable to the physician/surgeon using the biopsy needle as to the patient. The prior art has failed to recognize that the handles of a biopsy needle must securely engage into the physician's or surgeon's palm for optimum control of the instrument during a biopsy. It is also necessary that the stylet and cannula be engaged to each other during the biopsy process for providing total control to the physician or surgeon.

The present invention overcomes the disadvantages of prior art references by providing a biopsy needle having a winged handle and detent locking between the stylet and cannula.

SUMMARY OF THE INVENTION

The general purpose of the present invention is to provide a bone marrow biopsy needle having a cannula and a stylet, both of which engage and interlock with respect to each other, and which can be conveniently grasped by the physician or surgeon in the palm of the hand to provide secure control during the biopsy process.

According to one embodiment of the present invention, there is provided a biopsy needle having a cannula and stylet which interlock with each other, the cannula including a cannula having one end with at least one and preferably two formed members extending outwardly from the end, the other end having a swaged bevel ground and buffed tip providing sharp knife edges in the range of 30°-45° with respect to a molded housing, the molding housing molded about the formed members for securing thereto and including two vertically positioned hand wings of decreasing size extending outwardly therefrom, a button extending outwardly from an upward vertical member of reduced diameter with respect to the housing, and an internal bore extending through the housing to the top of the formed end of the cannula for accepting a syringe for drawing of bone marrow during the biopsy, and a stylet including one end having a bend for securing into a stylet cap and the other end having a beveled end in the range of 30°-60° and buffed to a polished end having a knife-sharp edge about the tip, the stylet cap secured about the bent end of the stylet and having a spring detent locking groove for engaging under and about the button of the cannula in a detented air-locking fashion, and an interior bore of a height to mate with the vertical member of the cannula and engage on the rim of the cannula formed between the housing and the vertical member whereby the stylet is engaged into the cannula housing and detent locks between the button on the cannula housing and the detent locking groove in the stylet cap providing for proper engagement between the knife-sharp edges of the cannula and the stylet, thereby providing for proper instrumentation during biopsy.

A significant aspect and feature of the present invention is a biopsy needle having wing-shaped handles facilitating gripping and engagement by the physician or surgeon user.

Another significant aspect and feature of the present invention is an interlocking stylet and cannula providing for not only interlocking of the structural members in a positive detent fashion but also predetermined orientation between the knife sharp edges of the cannula and the stylet. The interlocking structure also positions the stylet at a proper distance from the cannula, providing for consistent and secure biopsy surgery.

A further significant aspect and feature of the present invention is a bone marrow biopsy needle which can be constructed either as a disposable instrument or as a reusable instrument depending upon the type of molded material chosen for the cannula and stylet housings.

An additional significant aspect and feature of the present invention is a biopsy needle which can be constructed in different sizes for different sized individuals or for different applications.

Having described one embodiment of the present invention, it is the principal object hereof to provide a bone marrow biopsy needle including a cannula and stylet which interlock with each other. The disclosure also applies to needle structure per se, and is not to be construed as being limited to only biopsy needles, as other applications are inherent within the scope of this disclosure.

BRIEF DESCRIPTION OF THE DRAWINGS

Other objects and many of the attendant advantages of this invention will be readily appreciated as the same becomes better understood by reference to the following detailed description when considered in connection with the accompanying drawings, in which like reference numerals designate like parts throughout the figures thereof and wherein:

FIG. 1 illustrates a perspective view of a cannula and a stylet;

FIG. 2 illustrates a sectional view of the cannula;

FIG. 3 illustrates a sectional view of the stylet;

FIG. 4 illustrates a view of a biopsy needle including the engaged cannula and stylet; and, FIG. 5 illustrates an enlarged section of the cannula and stylet knife-sharp edges oriented with respect to each other.

DESCRIPTION OF PREFERRED EMBODIMENTS

FIG. 1 illustrates a perspective view of a biopsy needle 10 having separated components of a cannula member 12 and a stylet member 14. The cannula member 12 includes a longitudinal cannula 16 having a sharp knife edge 18 which has been swaged, beveled, ground and buffed as later described in detail, formed ends 20a and 20b illustrated in FIG. 2 extending outwardly at an angular tubular relationship, a molded housing 22 of ABS material or the like having the shape as illustrated and having molded thereto left-hand wing 24 and right-hand wing 26, a vertical member 28 extending upwardly, an elongated button 30 extending outwardly, and a chamber 32 running vertically downward from the top of member 28 to the top of the cannula 16 as also illustrated in FIG. 3. The stylet member 14 includes a metal stylet 34 having a sharp edge 36 which has been ground, buffed and polished, a bent end 38 for securing into a molded cap 40, a detent locking groove 42 having a spring member 44 including positive locking member 46. A downward extending boss 48 extends downwardly internal to the cap 40 for engagement with a rim 28a of the cannula housing 22. Locking vertical grooves 50 are provided about the cap for engagement by physician or surgeon user, and a rounded top 52 is provided for an individual's hand.

FIG. 2, which illustrates a cross-sectional view of the cannula member 12, shows the particular detail of the formed ends 20a and 20b securing the cannula 16 into the housing 22 about the vertical chamber 32 which decreases from a large diameter to a small diameter in a lure taper, then to a chamfer, and finally to a diameter which is slightly larger than the internal diameter of the cannula 16 so that a syringe can be inserted into the chamber 32 to draw bone marrow up into the cannula. A probe can be utilized to freely push the bone marrow out through the formed end of the cannula and onto a slide, without damaging or distorting the bone marrow. The detent button 30 and the rim 28a provide for engagement of the stylet member 14 in proper predetermined orientation. The particular detail of the tip 18 of the cannula is also illustrated providing that the angle between the vertical plane and the tip is in the range of 30°–45° and preferably 35° plus or minus 5°. The angle between the edge of the cannula and the vertical plane is 13½° plus or minus 1°. This tip structure 18 is obtained through swaging, beveling and grinding, and buffing to provide for a consistent tip for ease of surgery during the biopsy in a process later described in detail.

FIG. 3 illustrates a sectional view of the stylet member 14 where all numerals correspond to those elements previously described. The end of the stylet has an angle between horizontal and the edge of 45° plus or minus 2° while the angle may be in the range of 30°–60°. The tip is buffed and polished to maintain a sharp knife edge. The upper end 38 of the stylet 34 is bent for securing into the cap 40.

MODE OF OPERATION

FIG. 4 illustrates the biopsy needle 10 of the present invention where the stylet member 14 is engaged and interlocked to the cannula member 12. The detent button 30 provides for locking of the members 12 and 14 together by engagement through the groove 42, and up and over the spring member 44 into the positive locking detent 46. A spring member 44 provides a positive sensory digital feedback signal that the members are engaged where button 30 resides in the chamber area of positive locking member 46. The button 30 and positive locking chamber 46 always provide that the knife edges 18 of the cannula 16 and 36 of the stylet 34 are always oriented with respect to each other as illustrated in the figure, and as also illustrated in FIG. 5, providing least minimum effort on the physician's/surgeon's part during the biopsy surgery. The boss 48 of the stylet member 14 seats the stylet onto the cannula at a proper predetermined distance and provides for the orientation of the knife edges. The beveled tips of the stylet and cannula provide for the proper cutting action through the bone due to the wedge action of the tips. The particular angles of the wedges and orientation with respect to each other is one of the keys to obtaining a suitable bone marrow sample during the biopsy process. The contour of the handles 24 and 26 and the winged configuration provide for positive feel to the physician/surgeon during the biopsy. The formed ends 20a and 20b secure the cannula 16 into the housing 22, and maintain round configuration of the cannula tube end 16 in the housing 22, providing for passage of a sample without damaging or distorting the sample.

The end 18 of the cannula 16 is processed according to the predetermined relationship set forth below where:

offset = ½ (tan (bevel angle).tan(tip angle).(I.D.)) and where I.D. is internal diameter of the cannula 16 and offset is the distance between the grinding centerline and the cannula tube centerline.

In processing the cannula, first the cannula is formed at the housing end and then swaged over a mandrel to a predetermined internal diameter over a predetermined length from the lower end. Then the cannula is eccentrically rotated about the offset centerline and ground at the same time to achieve the 35° plus or minus 5° tip angle in conjunction with 13½° plus or minus 1° chamfer beveled angle. The beveling of the edge is done at specific orientation to the housing as illustrated in FIG. 2 of the drawing to obtain the predetermined result. After the rotating and grinding operation, the end is buffed and blended to the sharp knife edge for achieving the product by process as illustrated in FIG. 5.

Various modifications to the biopsy needle of the present invention can be made without departing from the apparent scope thereof. The disclosure is applicable to generic needles and is not to be construed as being limited to biopsy needles. The disclosure is applicable to attachment on a needle to structure in general and for forming a predetermined tip at the end of the needle.

Having thus described the invention, what is claimed is:

1. A biopsy needle comprising:
   a. tubular cannula means including a longitudinal cannula with a knife sharp edge, said tubular cannula means including handle means for handily supporting said tubular cannula means, said handle means including a truncated conical member secured about an upper portion of said tubular cannula means and opposing vertically oriented handle wings extending outward from said truncated conical member, a rim cylindrical member positioned on said truncated conical member, and means for interlocking extending outward on said rim, said interlocking means including a button projection;

b. stylet means for engaging into said tubular cannula means and protruding forward of said tubular cannula means for piercing through skin, flesh, muscle and bone, including a sharpened angled edge and cap means having supporting positive detent interlocking means for engaging or twisting with said interlocking means of said sample means oriented by said engagement of said interlocking means within said positive detent interlocking means on said cap means, said cap means supporting said stylet means; and c. said beveled edge of said tubular cannula means and said edge of said stylet means being substantially aligned on a vertical axis with respect to each other, said knife-sharp edge of said cannula has an angular tip relationship so that the offset of the cannual wall satisfies $\frac{1}{2}$(tan (bevel angle) tan(tip angle) (I.D. cannula tube)) whereby said tubular cannula means and said stylet means engage in predetermined oriented relationship with said interlocking means and said positive detent interlocking means thereby provide a positive detent interlocking between said sample means and said protruding means for taking a biopsy sample.

2. Needle of claim 1 wherein said beveled edge has a 35° plus or minus 5° with respect to the horizontal.

3. Needle of claim 2 wherein said edge is 13½° plus or minus 1° with respect to the vertical.

4. Needle of claim 3 wherein said sharp edge of said stylet means is 45° plus or minus 2°.

5. Needle of claim 1 wherein said stylet means include a bent end for securing into said cap means, said cap means being molded.

6. Needle of claim 1 wherein said tubular cannula means includes at least one formed outwardly extending taper member for securing into said truncated conical member.

7. Needle of claim 6 comprising at least two formed outwardly extending tapers.

8. Needle of claim 1 wherein said engaging means comprises a detent locking groove.

9. Needle of claim 8 wherein said detent locking groove is spring biased.

10. Needle of claim 1 wherein said button projection is elongated.

* * * * *